United States Patent [19]

Chalmers

[11] Patent Number: 5,039,228
[45] Date of Patent: Aug. 13, 1991

[54] FIXTURELESS ENVIRONMENTAL STRESS SCREENING APPARATUS

[75] Inventor: Richard H. Chalmers, San Diego, Calif.

[73] Assignee: The United States of America as represented by the Secretary of the Navy, Washington, D.C.

[21] Appl. No.: 431,341

[22] Filed: Nov. 2, 1989

[51] Int. Cl.$^5$ .................. G01N 25/72; G01N 25/00; G01N 29/00; G01N 33/00
[52] U.S. Cl. .......................... 374/57; 374/5; 374/141; 374/142; 73/865.6; 73/662; 73/571
[58] Field of Search .............. 374/4, 5, 57, 45, 50, 374/141, 142; 73/571, 577, 579, 582, 671, 662, 865.6

[56] References Cited

U.S. PATENT DOCUMENTS

| H229 | 3/1987 | Phillips | 73/865.6 |
|---|---|---|---|
| 2,523,322 | 9/1950 | Ornstein et al. | 374/57 |
| 3,273,802 | 9/1966 | Hull, Jr. | 73/865.6 |
| 3,327,536 | 6/1967 | Fitzgerald | 73/865.6 |
| 3,365,930 | 1/1968 | Arias | 73/15 |
| 4,092,869 | 6/1978 | Kimball | 374/57 |
| 4,519,718 | 5/1985 | Staffin et al. | 374/45 |
| 4,575,257 | 3/1986 | Ogura et al. | 374/57 |
| 4,729,246 | 3/1988 | Melgaard et al. | 73/865.6 |
| 4,733,973 | 3/1988 | Machak et al. | 374/57 |
| 4,787,752 | 11/1988 | Fraser et al. | 374/45 |
| 4,812,750 | 3/1989 | Keel et al. | 324/158 F |
| 4,817,447 | 4/1989 | Kashima et al. | 73/865.6 |
| 4,854,726 | 8/1989 | Lesley et al. | 374/57 |
| 4,879,905 | 11/1989 | Chen et al. | 73/579 |
| 4,955,726 | 9/1990 | Bargigia et al. | 374/57 |

FOREIGN PATENT DOCUMENTS

| 0184943 | 11/1982 | Japan | 73/865.6 |
|---|---|---|---|
| 0263836 | 12/1985 | Japan | 374/57 |
| 0087827 | 4/1987 | Japan | 374/57 |
| 0212836 | 9/1988 | Japan | 73/865.6 |
| 0212837 | 9/1988 | Japan | 73/865.6 |
| 0274039 | 11/1989 | Japan | 374/57 |
| 8704526 | 7/1987 | World Int. Prop. O. | 374/57 |

OTHER PUBLICATIONS

Gunn, J. E. et al., "Highly Accelerated Stress Test," IBM Technical Disclosure Bulletin, vol. 24, No. 4 (Sep. 1981).
Iowa Air Crash Laid to Metallurgical Flaw by Paul Houston, Oct. 29, 1989, Los Angeles Times, Los Angeles, CA.

Primary Examiner—William A. Cuchlinski, Jr.
Assistant Examiner—Diego F. F. Gutierrez
Attorney, Agent, or Firm—Harvey Fendelman; Thomas Glenn Keough; Peter A. Lipovsky

[57] ABSTRACT

A fixtureless environmental screening device is provided for the testing of mechanical, electromechanical and electrical devices. The apparatus uses a relatively incompressible fluid having a high heat capacity and a high heat of vaporization to transfer heat and vibration to a device to be tested. The heat transfer characteristics of the fluid permits a device tested to undergo rapid temperature change while being simultaneously subjected to vibrational cycling. By utilizing a fluid as a vibration transmission medium expensive fixtures are avoided so that devices of a wide variety of shapes and sizes may be readily tested. The dielectric properties of the working fluid permits energization of electrical devices during the course of vibration and temperature cycling.

39 Claims, 2 Drawing Sheets

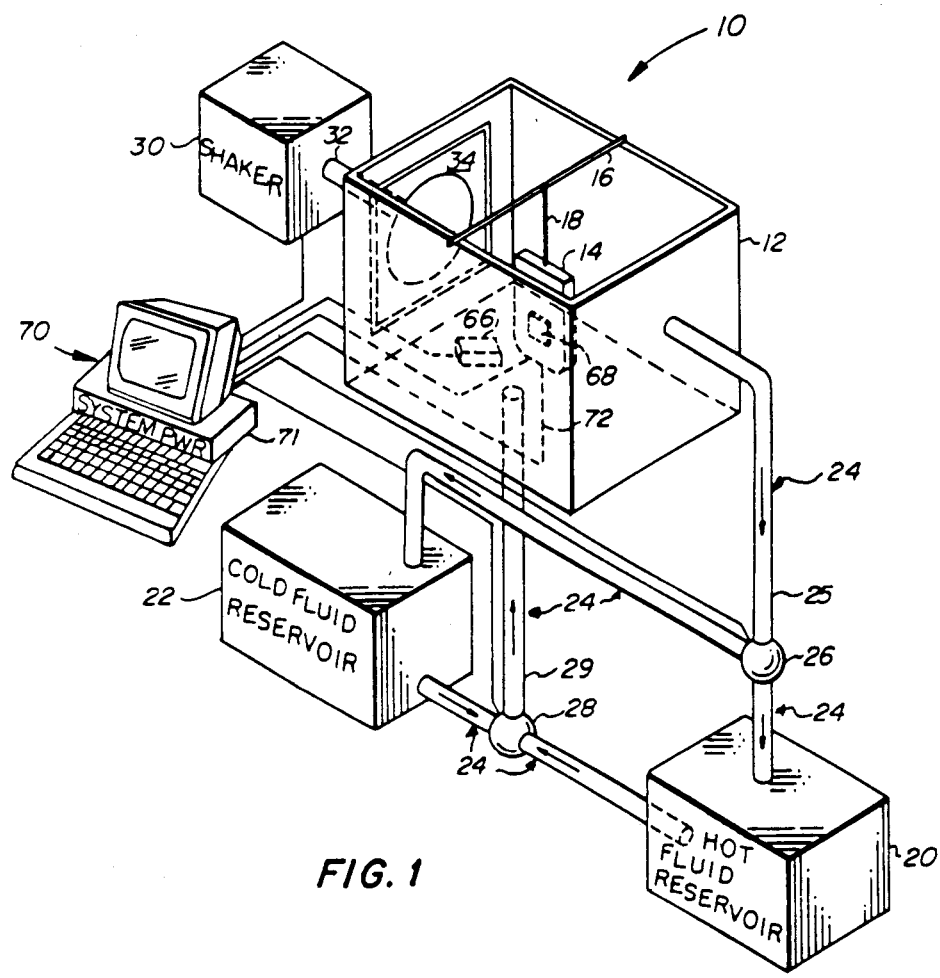
FIG. 1
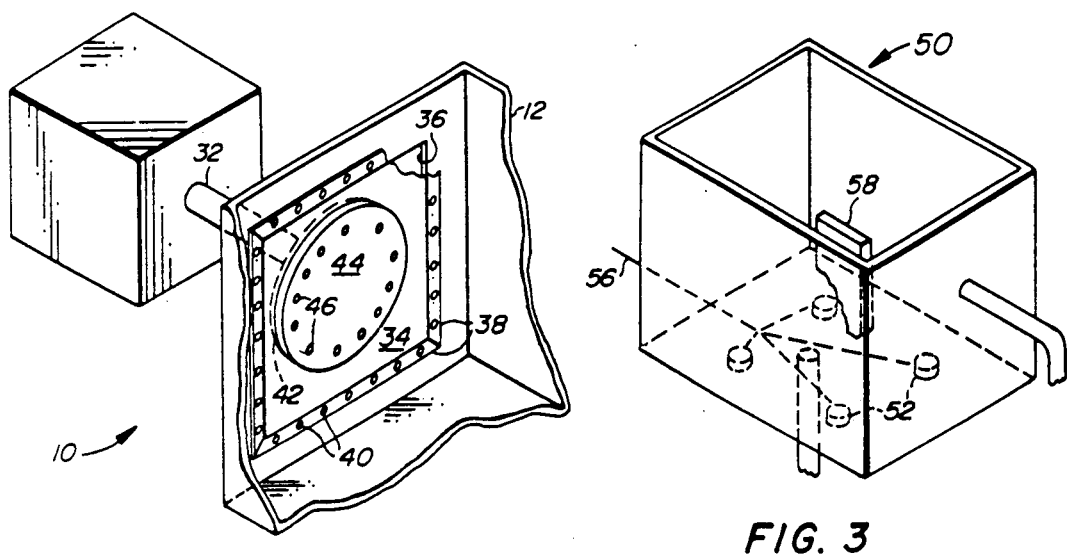
FIG. 2
FIG. 3

FIXTURELESS ENVIRONMENTAL STRESS SCREENING APPARATUS

Statement of Government Interest

The invention described herein may be manufactured and used by or for the Government of the United States of America for governmental purposes without the payment of any royalties thereon or therefor.

BACKGROUND OF THE INVENTION

1. Field of the Invention

This invention relates to environmental screening apparatuses such as those that subject mechanical electromechanical and electrical devices to a variety of environments designed to reveal defects in the devices.

2. Description of the Prior Art

Environmental stress screening is a process by which environmental stresses are applied to recently manufactured devices to disclose defects in the devices that would not otherwise be exposed by more common techniques such as visual examination. If defects go undiscovered at the point of manufacture they may eventually reveal themselves in the field where repair of the device can cost hundreds of times the cost of repair at the point of production.

Over the past few years environmental stress screening of electrical devices has reached the state where the process consists of an average of 12 minutes of random vibration and of 20 cycles of temperature changes. Where feasible, electrical devices are cyclically energized by repetitively turning the devices on and off at the same or varying power levels.

Apparatuses for vibration screening devices often require custom made fixtures to attach the devices to the apparatuses. As the size and shape of the device to be tested changes, the fixture must be changed or redesigned accordingly. The expense of these changes is ultimately added to the production cost of the device.

Some prior art vibration screening apparatuses suffer not only from the above shortcoming but also are ineffective in transmitting controlled vibration to the device to be tested. This may be due to an inadequate area of force transmittal between the fixture and the device or may be due to a mismatch between the mass of the fixture and the production device or even a combination of these.

The problems of the prior art vibration screening apparatuses are exasperated when large items, such as those greater than or equal to 12 inches on a side, are tested. Frequently it is necessary to fabricate custom made fixtures for these items and it is common that a single vibration driver will not be suitably effective in vibrating the item.

Multiple drivers can be used but of course this adds further to the cost of the item. As a result, larger items are often exempted from vibration screening or they receive vibration exposures very much reduced in effectiveness.

Temperature cyclical screening facilities typically use air to transfer heat to and from the item to be tested. Though it is now becoming more widely understood that to effectively temperature screen electrical devices rapid temperature changes approaching 20 degrees Celsius per minute are needed, most air chambers provide temperature change rates of only about 2.5 degrees Celsius per minute.

For small items, it is possible to achieve rapid temperature cycling by using hot-air and cold-air climatic chambers and moving the item from one chamber to the other. For larger items the difficulty in changing chambers is outweighed by the advantage, so that the reduced efficiency of a slow rate of temperature change is accepted.

In many cases it is desirable to energize an electrical item while it is being subject simultaneously to vibration and temperature environments. When electrical items are shuffled between chambers, cyclicly energizing the item can prove to be difficult. Electrical connections must be sufficiently long and there is the potential for electrical shock or accidental circuit grounding.

If an electrical device is energized in a hot air environment it can sometimes generate local areas of heating that exceed the proposed upper temperature limit of the device. Even if forced convection is used, the air can be insufficient in carrying heat away from the locally heated regions so that destruction of both flawed and flawless devices may occur.

Under the ideal test conditions, a device will be subjected to conditions that approach as near as possible those conditions the device is expected to go through during its normal duty cycle. It is also desirable to subject devices to certain extremes beyond those of normal environments to accelerate the "surfacing" of production flaws that would not otherwise be detected.

In either case test screening apparatuses should be able to subject a device to multitude of test screenings at once.

Some prior art schemes exist in which temperature cycling and vibration are combined. Others combine device energization and temperature cycling. Generally, both of these established methods suffer from the shortcomings described above.

A need therefor exists for an environmental screening apparatus that subjects a device to simultaneous temperature, vibrational and, where applicable, energization cycles while at the same time avoids the expensive fixtures, multiple chambers, and ineffectual heat transfer of the prior art.

SUMMARY OF THE INVENTION

The invention provides a way of overcoming the shortcomings of the prior art by providing an environmental screening facility that obviates the need for expensive fixtures, does away with the need for transferring a device from vat to vat or chamber to chamber and provides for efficient and rapid temperature changes. This environmental screening facility provides for simultaneous vibration, temperature and, where applicable, energization cycling of a device to be tested.

The invention utilizes a single test vessel in which a device to be tested is placed. Reservoirs of hot and cold liquids are coupled to the test vessel by a circulative channel so that a hot, cold or combination temperature liquid may be rapidly dispensed into and out of the vessel. Using this system, device or devices within the vessel may be subject to rapid temperature changes approximating 120 degrees Celsius per minute.

To simultaneously couple vibrational forces to the device a wall of the test vessel is made of a flexible material that is externally coupled to a electromechanical transducer or shaker. The oscillating movement of the shaker is carried to the liquid within the chamber by the corresponding movement of the flexible wall. Alternative versions include transducers that are attached directly to the vessel or that are placed within the fluid surrounding the device. In both cases the transducers generate the desired vibrational forces within the liquid and hence within the device to be tested.

Simultaneous energization of electrical devices is made possible by the dielectric properties of the working fluid. This energization is made easy as the device may remain within a single vessel throughout its testing. Further, the heat transfer characteristics of the working fluid substantially prevents the generation of local hot spots and device overheating during device energization.

To closely ascertain test conditions a thermal monitor and a motion detector may be utilized and these may be coupled to a computer control so that test adjustments may be made by either operator interaction or through programmed steps. The proportioning of the hot and cold liquids as well as device energization, shaker frequency and vibration duration may be controlled by way of the computer.

OBJECTS OF THE INVENTION

It is an object of the invention to provide an apparatus for detecting flaws or defects in devices of mechanical, electromechanical and electrical nature.

Another object of the invention is to provide an environmental screening apparatus that permits both large and small devices to be subjected to rapid temperature cycling.

Yet another object of the invention is to provide an apparatus for temperature cycling a device to be tested without the need to transfer the device during the course of the test.

It is another object of the invention to provide an apparatus that simultaneously subjects a device to be tested to vibration and temperature cycling.

Another object of the invention is to provide an apparatus that permits simultaneous temperature and vibration cycling of a device to be tested without the need for customized attachment fixtures.

Yet another object of the invention is to provide an improved environmental screening apparatus for simultaneously subjecting electrical devices to changes of temperature, vibration and energization without the need for custom made attachment fixtures, multiple climatic chambers and multiple vibrators.

These and other objects, advantages and new features of the invention will become apparent from the following detailed description of the invention when considered in conjunction with the accompanied drawings.

BRIEF DESCRIPTION OF THE DRAWINGS

FIG. 1 is a schematic representation of a fixtureless environmental screening apparatus according to the invention.

FIG. 2 is a detail view of a portion of FIG. 2.

FIG. 3 is a portion of an alternative embodiment of the invention in which transducers are attached directly to a test vessel in which a device to be tested is placed.

DESCRIPTION OF THE PREFERRED EMBODIMENT

Figure 4:
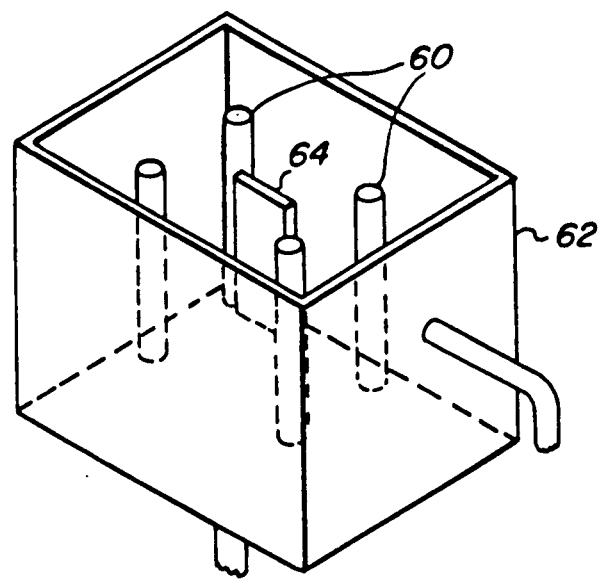
FIG. 4 is a portion of another embodiment of the invention in which transducers are placed directly within a fluid surrounding a device to be tested.

Referring to FIG. 1 there is shown a schematic representation of a fixtureless environmental screening apparatus 10 according to the invention. Apparatus 10 includes a vessel 12 in which a device 14, such as one of a mechanical, electromechanical or electrical nature, is disposed. Device 14 is preferably suspended within vessel 12 by appropriate structure such as by suspension rod 16 and cable 18.

A reservoir of hot fluid 20 and a reservoir of cold fluid 22 are coupled to vessel 12 so that the contained fluids may be dispensed into the vessel. Appropriate pumping equipment, not shown, can be utilized where necessary to create sufficient fluid pressure.

In a preferred embodiment of the invention fluids within reservoirs 20 and 22 are passed to and from vessel 12 by way of a circulative channel 24. In FIG. 1, arrows are shown to illustrate one possible path by which these fluids may flow. Through the path shown, draining of vessel 12 takes place through channel member 25 and valve 26 to flow into either reservoir 20 and/or reservoir 22 with the filling of vessel 12 from reservoir 20 and/or reservoir 22 occurring through valve 28 and channel member 29. Circulative channel 24 permits the fluids within reservoirs 20 and 22 to be rapidly exchanged within vessel 12 to enable device 14 to undergo rapid temperature changes as will be further explained. These rapid temperature changes or cycles are used to reveal flaws within the device that may not otherwise be detected until the device is put into field use.

As previously discussed, many prior art environmental screening facilities utilized air as a heat transfer medium. These climatic chambers provide temperature change rates of about 2-½ degrees Celsius per minute. In accordance with a preferred embodiment of the invention, perfluorinated liquid having a relatively high heat capacity, when compared to air, is utilized in the invention. Such a fluid is available under the trademark "FLUORINERT" and is manufactured by Minnesota Mining and Manufacturing Corporation of St. Paul, Minn.

The perfluorinated liquid has approximately 1667 times the heat absorbing capacity of an equal volume of air and is stable over a wide range of temperatures, having a pour point of $-50$ degrees Celsius and a boiling temperature of 174 degrees Celsius. When the perflourinated liquid is circulated sufficiently through vessel 12 temperature changes within the vessel of approximately 120 degrees Celsius per minute are possible.

In a preferred embodiment of the invention hot reservoir 20 and cold reservoir 22 contain "FLUORINERT" at 70 degrees and minus 20 degrees Celsius, respectively. These temperatures were chosen to expose electrical devices such as printed wiring boards and printed wiring assemblies to temperature change rates of 10 to 20 degrees Celsius per minute. Of course the particular temperatures of the fluids used and the change rates desired may be varied as it may be determined that other temperatures and change rates are more effective in revealing device workmanship flaws.

The use of perfluorinated liquid permits a limiting of device upper temperatures as device overheating is prevented by the vapor phase cooling of this high heat capacity liquid. This is particularly useful where electrical components are subjected to elevated temperatures while simultaneously being energized, thereby developing the potential of forming local "hot spots" within the component. In air climatic chambers, the relatively low heat capacity of the air may not sufficiently transfer the heat from local hot spots before a deterioration of the device is experienced.

Circulative channel 24 provides a means by which fluids from reservoirs 20 and 22 may be rapidly circulated within vessel 12 so that device 14 may be exposed to relatively large temperature changes in relatively short periods of time. Valves 26 and 28 are used to proportion flow between the reservoirs and the vessel. The valves are preferably electromechanical and may be coupled to a computer to allow operator or preprogrammed interaction to control the valves as will be discussed.

By utilizing reservoirs of fluid maintained at temperature extremes and by piping these fluids into a vessel in which the device is to be tested, it becomes unnecessary to transfer the device from one chamber or vat to a second chamber or vat in order to expose the device to varying temperatures. This is particularly useful where large devices are tested, as the difficulty in transferring the devices from one climate to another may result in unwanted delays between exposures.

To simultaneously expose device 14 to vibration as well as temperature environments the fluid within vessel 12 is used as a transmission medium between device 14 and the oscillating movement of an electromechanical transducer 30. Transducer 30, otherwise known as a shaker, has an oscillating member 32 that reciprocates at desired preselected frequencies. This oscillating member is coupled to vessel 12 by a flexible diaphragm 34.

Referring to FIG. 2 a detail view of a portion of apparatus 10 is shown in which flexible diaphragm 34 is further illustrated. Flexible diaphragm 34 covers a hole 36 defined in a side of vessel 12 and is sealed and attached to vessel 12 by conventional structure such as frame members 38 and fasteners 40. To couple the mechanical motion of oscillating member 32 to flexible diaphragm 34 a plate 42, shown in phantom lines, is fastened to the member and is placed against the exterior side of flexible diaphragm 34. A plate 44 corresponding to plate 42 is placed along the interior surface of diaphragm 34 and is attached to plate 42 by conventional fasteners 46 that protrude through diaphragm 34 in a sealing relationship.

Referring now to both FIGS. 1 and 2 the reciprocating motion of flexible diaphragm 34 is passed to device 14 through the fluid within vessel 12. Coupling vibratory motion to a device in this manner obviates the need for the expensive fixtures otherwise necessary to attach the device to the transducer or shaker. Obviously this will make it easy to use apparatus 10 with devices of a great variety of shapes and sizes. For devices of an electronic nature, this means that individual components, slide mounted drawers, six foot racks and even multi-bay cabinets, for example, could be tested. The tests are limited only by the size of the vessel in which the device is placed and the power of the vibration source used.

By coupling vibratory motion to a device through a fluid medium, vibratory motion can be applied over a large area of the device. Damage which might otherwise be caused by fixtures being attached to only a small portion of the device or because of a severe mismatch between the mass of the device and the fixture used is thus avoided.

Because of the difference in the manner of introducing vibratory motion to the device, oscillatory pressure over the entire surface of the device contrasted to coupling motion through a select few points of the device, it is believed that the vibratory compressive stress experienced by devices being fluid screened may reveal latent defects in the devices that would otherwise not be brought to light with conventional vibration screening apparatuses.

These vibratory compressive stresses could be transmitted not only to a single device, as shown in FIG. 1, but could be passed to a plurality of devices, provided that sufficient spacing is permitted between the devices to permit ample vibration transmission. In either case the device or devices may be rotated within the test vessel to achieve a desired exposure. These devices need not be suspended within the test vessel as shown but may be supported in other ways that permit the devices to be exposed to the moving liquid.

Satisfactory service of apparatus 10 has been obtained with a single transducer however those skilled within the art will realize that multiple transducers could be incorporated with the apparatus providing that vibration cancellation and resonance are considered. These transducers, for example, may be placed directly within the working fluid within the test vessel or may be attached directly to the vessel itself.

FIG. 3 is a partial view of an alternative embodiment of the invention in which apparatus 50 has four piezoelectric transducers 52 attached directly to an underside of a test vessel 54. In a well understood manner the absence or presence of electrical impulses applied to piezoelectric elements 52, such as by way of electrical connection 56, causes the elements to expand or contract. This motion is imparted to vessel 54 so that any fluid therein experiences these movements and transmits them to a device 58 suspended within the vessel by structure not shown.

In FIG. 4, a partial view of another embodiment of the invention is shown in which transducer elements 60 are placed directly within the working fluid filling test vessel 62. Transducers 60 can be suspended by any conventional means, not shown, and are energized with electronic impulses to cause the transducers to expand and contract in a well understood way. The movements of the transducers are passed to the fluid surrounding a device 64, to vibrationally test the device.

Referring once again to FIG. 1 it can be seen that a thermal sensor 66 can be used to monitor the temperature changes of any fluid within the test vessel. In addition, a motion detector 68 can be attached to a device being tested so that the motion of the device can be monitored. A typical pressure transducer could be used for this purpose.

In FIG. 1 a computer 70 is shown incorporated with apparatus 10 and is operably connected to electromechanical proportioning valves 26 and 28, transducer 30, thermal monitor 66, motion detector 68 and energization cable 72 of device 14. Computer 70 includes power supplies, within housing 71, that provide power to energize and actuate system components. Of course these power supplies may be positioned independently of computer 70 at other locations within the system.

Those skilled in the art will realize that such a computer, such as an International Business Machine Corporation personal computer or equivalent, may be appropriately programmed and equipped to be utilized in any of the embodiments of the invention to monitor testing, provide operator control as well as to provide a preprogrammed sequence of test operations so that device testing may be performed autonomously.

It should be noted that though a perfluorinated liquid such as "FLUORINERT" has been used in a preferred embodiment of the invention other fluids such as water or ethylene glycol, for example, may be utilized with the invention. Of course the thermal characteristics of these fluids would have to be investigated to determine whether preselected temperature extremes and changes can be reached. To alter the heating characteristics of the fluid used, those skilled in the art will realize that the test vessel could be closed and pressurized.

The fixtureless environmental screening apparatus of the invention permits devices large and small of mechanical, electromechanical and electrical nature to be vibrationally tested without the need for custom made associated fixtures. The apparatus also permits the simultaneous temperature cycling of a device through a wide range of rapid temperature changes without the need for transferring the device from one chamber to another. By performing all vibration and temperature cycling within a single vessel, energization of electrical devices is made easy as lengthy cables or the need for disconnection and connection is obviated.

Obviously, many modifications and variations of the invention are possible in light of the above teachings. It is therefore to be understood that within the scope of the appended claims the invention may be practiced otherwise than as has been specifically described.

What is claimed is:

1. An apparatus for thermally and vibrationally testing a device comprising:
   a vessel in which said device is placed;
   means for selectively dispensing a cold liquid into said vessel to thermally test said device;
   means for selectively dispensing a hot liquid into said vessel to thermally test said device;
   means for transmitting vibratory motion directly to said device through any liquid placed within said vessel to vibrationally test said device; and
   means for selectively draining said any liquid from said vessel.

2. An apparatus according to claim 1 in which said device is an electrical device.

3. An apparatus according to claim 2 further including:
   means for selectively energizing said electrical device.

4. An apparatus according to claim 1 in which said cold liquid is at a temperature that is below the freezing point of water.

5. An apparatus according to claim 4 in which said cold liquid and said hot liquid differ by a temperature of at least 40 degrees Celsius.

6. An apparatus according to claim 5 in which said cold liquid and said hot liquid are a perfluorinated liquid.

7. An apparatus according to claim 1 in which said means for transmitting vibratory motion to said any liquid placed within said vessel includes a transducer that converts electrical power into mechanical motion.

8. An apparatus according to claim 7 in which said transducer includes a piezoelectric element, said piezoelectric element being attached to said vessel.

9. An apparatus according to claim 7 in which said transducer is suspended within said vessel so that said any liquid placed within said vessel makes contact with said transducer.

10. An apparatus according to claim 7 in which said means for transmitting vibratory motion to said any liquid placed within said vessel includes an electrically driven shaker having an oscillating member coupled to a flexible bladder that covers an opening defined in said vessel.

11. An apparatus for testing electrical, electromechanical and mechanical devices comprising:
   a vessel in which a device to be tested is placed;
   a reservoir of below-zero degree Celsius liquid;
   a reservoir of above-zero degree Celsius liquid,
   said below-zero degree Celsius liquid and said above-zero degree Celsius liquid differing in temperature by at least 40 degrees Celsius,
   means disposed between said vessel and each of said reservoirs for piping said below-zero degree Celsius liquid and said above-zero degree Celsius liquid between said reservoirs and said vessel;
   means for controlling the flow of said below-zero degree Celsius liquid and said above-zero degree Celsius liquid between said reservoirs and said vessel;
   means for transmitting vibratory motion to said device directly through any liquid piped into said vessel; and means for selectively draining said any liquid within said vessel from said vessel.

12. An apparatus according to claim 11 further comprising means for selectively energizing an electrical device to be tested and an electromechanical device to be tested.

13. An apparatus according to claim 11 in which said means for transmitting vibratory motion to said device through said any liquid piped into said vessel includes an electromechanical transducer coupled to a flexible diaphragm that covers an opening defined in a wall of said vessel so that vibratory motion of said electromechanical transducer is coupled to said any liquid within said vessel by said flexible diaphragm responding to motion imparted to it by said electromechanical transducer.

14. An apparatus according to claim 11 in which said means for transmitting vibratory motion to said device through any liquid piped into said vessel includes a piezoelectric element attached to said vessel.

15. An apparatus according to claim 11 in which said means for transmitting vibratory motion to said device through said any liquid piped into said vessel includes a transducer that is suspended within said vessel so that said any liquid placed within said vessel makes contact with said transducer.

16. An apparatus according to claim 11 in which said below-zero degree Celsius liquid and said above-zero degree Celsius liquid are a perfluorinated liquid.

17. An apparatus for testing a device comprising:
   a vessel in which said device is placed;
   a reservoir of cold fluid coupled to said vessel so that said cold fluid may be selectively dispensed into said vessel;
   a reservoir of hot fluid coupled to said vessel so that said hot fluid may be selectively dispensed into said vessel;
   a flexible diaphragm that covers an opening defined in a surface of said vessel;
   an electromechanical transducer coupled to said flexible diaphragm so that vibratory motion of said electromechanical transducer is coupled to any fluid within said vessel; and
   a valve coupled to said vessel for selectively draining at least a portion of said any fluid within said vessel from said vessel.

18. An apparatus according to claim 17 in which said device is an electrical device.

19. An apparatus according to claim 18 further including a power source for selectively energizing said electrical device.

20. An apparatus according to claim 19 in which said electrical device is part of a printed wiring assembly.

21. An apparatus according to claim 20 in which said printed wiring assembly is part of a rack.

22. An apparatus according to claim 21 in which said rack is part of a multi-bay cabinet.

23. An apparatus according to claim 17 in which said cold fluid is at a temperature that is less than the freezing point of water.

24. An apparatus according to claim 23 in which said cold fluid and said hot fluid differ in temperature by at least 40 degrees Celsius.

25. An apparatus according to claim 24 in which said cold fluid and said hot fluid differ in temperature by at least 70 degrees Celsius.

26. An apparatus according to claim 25 in which said cold fluid and said hot fluid are a single fluid differing only in temperature, said single fluid having a relatively high heat capacity compared to air.

27. An apparatus according to claim 26 in which said single fluid is a perfluorinated liquid.

28. An apparatus according to claim 27 in which said perfluorinated liquid is known by the trademark name "FLUORINERT".

29. An apparatus for testing electrical, electromechanical and mechanical devices comprising:
a vessel in which a device to be tested is placed;
a reservoir of below-zero degree Celsius fluid;
a reservoir of above-zero degree Celsius fluid,
said below-zero degree Celsius fluid and said above-zero degree Celsius fluid differing in temperature by at least 40 degrees Celsius,
means disposed between said vessel and each of said reservoirs for piping said below-zero degree Celsius fluid and said above-zero degree Celsius fluid between said reservoirs and said vessel;
means for controlling the flow of said below-zero degree Celsius fluid and said above-zero degree Celsius fluid between said reservoir and said vessel;
a temperature sensor disposed within said vessel for sensing the temperature of any fluid within said vessel;
means for transmitting vibratory motion directly to said any fluid piped into said vessel, wherein said vibratory motion is transmitted through said any fluid to said device;
a motion detector operably coupled to any device to be tested to detect vibrational movement of said device;
means for selectively energizing an electrical device to be tested and an electromechanical device to be tested; and
means for selectively draining said any fluid within said vessel from said vessel.

30. An apparatus according to claim 29 in which said motion detector is a pressure transducer.

31. An apparatus according to claim 29 in which said means for controlling the flow of said below-zero degree Celsius fluid and said above-zero degree Celsius fluid between said reservoirs and said vessel includes electromechanical valves individual to said reservoirs, said electromechanical valves being operably coupled to said means for piping said below-zero degree Celsius fluid and said above-zero degree Celsius fluid.

32. An apparatus according to claim 31 further including a computer control means for monitoring and controlling said means for transmitting vibratory motion directly to said any fluid piped into said vessel, said means for selectively energizing said electrical device and said electromechanical device, said temperature sensor, said motion detector and said electromechanical valves.

33. An apparatus for thermally and vibrationally testing a device comprising:
a vessel in which said device is placed;
means for selectively dispensing cold FLUORINERT liquid into said vessel to thermally test said device, said cold FLUORINERT liquid being at a temperature that is below the freezing point of water;
means for selectively dispensing hot FLUORINERT liquid into said vessel to thermally test said device, in which said cold FLUORINERT liquid and said hot FLUORINERT liquid differ by a temperature of at least 40 degrees Celsius;
means for transmitting vibratory motion directly to any FLOURINERT liquid placed within said vessel to vibrationally test said device, wherein said vibratory motion is transmitted through said any FLOURINERT liquid to said device; and
means for selectively draining said any FLOURINERT liquid from said vessel.

34. An apparatus for thermally and vibrationally testing a device comprising:
a vessel in which said device is placed;
means for selectively dispensing a cold fluid into said vessel to
thermally test said device, said cold fluid being at a temperature that is below the freezing point of water;
means for selectively dispensing a hot fluid into said vessel to thermally test said device;
means for transmitting vibratory motion directly to any fluid placed within said vessel to vibrationally test said device, wherein said vibratory motion is transmitted through said any fluid to said device, said means including a piezoelectric element transducer attached to said vessel for converting electrical power into mechanical motion; and
means for selectively draining said any fluid from said vessel.

35. An apparatus for thermally and vibrationally testing a device comprising;
a vessel in which said device is placed;
means for selectively dispensing a cold fluid into said vessel to thermally test said device, said cold fluid being at a temperature that is below the freezing point of water;
means for selectively dispensing a hot fluid into said vessel to thermally test said device;
means for transmitting vibratory motion directly to any fluid placed within said vessel to vibrationally test said device, wherein said vibratory motion is transmitted through said any fluid to said device, said means including a transducer that converts electrical power into mechanical motion and that is suspended within said vessel so that any fluid placed within said vessel makes fluid contact with said transducer; and
means for selectively draining said any fluid from said vessel.

36. An apparatus for thermally and vibrationally testing a device comprising:
- a vessel in which said device is placed;
- means for selectively dispensing a cold fluid into said vessel to thermally test said device, said cold fluid being at a temperature that is below the freezing point of water;
- means for selectively dispensing a hot fluid into said vessel to thermally test said device;
- means for transmitting vibratory motion directly to any fluid placed within said vessel to vibrationally test said device, wherein said vibratory motion is transmitted through said any fluid to said device, said means including an electrically driven shaker having an oscillating member coupled to a flexible bladder that covers an opening defined in said vessel; and
- means for selectively draining said any fluid from said vessel.

37. An apparatus for testing electrical, electromechanical and mechanical devices comprising:
- a vessel in which a device to be tested is placed;
- a reservoir of below-zero degree Celsius fluid;
- a reservoir of above-zero degree Celsius fluid,
- said below-zero degree Celsius fluid and said above-zero degree Celsius fluid differing in temperature by at least 40 degrees Celsius,
- means disposed between said vessel and each of said reservoirs for piping said below-zero degree Celsius fluid and said above-zero degree Celsius fluid between said reservoirs and said vessel;
- means for controlling the flow of said below-zero degree Celsius fluid and said above-zero degree Celsius fluid between said reservoirs and said vessel;
- means for transmitting vibratory motion directly to any fluid piped into said vessel including an electromechanical transducer coupled to a flexible diaphragm that covers an opening defined in a wall of said vessel so that vibratory motion of said electromechanical transducer is coupled to said any fluid within said vessel by said flexible diaphragm responding to motion imparted to it by said electromechanical transducer, wherein said vibratory motion is transmitted through said any fluid to said device;
- means for selectively energizing an electrical device to be tested and an electromechanical device to be tested; and
- means for selectively draining said any fluid within said vessel from said vessel.

38. An apparatus for testing electrical, electromechanical and mechanical devices comprising:
- a vessel in which a device to be tested is placed;
- a reservoir of below-zero degree Celsius fluid;
- a reservoir of above-zero degree Celsius fluid,
- said below-zero degree Celsius fluid and said above-zero degree Celsius fluid differing in temperature by at least 40 degrees Celsius,
- means disposed between said vessel and each of said reservoirs for piping said below-zero degree Celsius fluid and said above-zero degree Celsius fluid between said reservoirs and said vessel;
- means for controlling the flow of said below-zero degree Celsius fluid and said above-zero degree Celsius fluid between said reservoirs and said vessel;
- means for transmitting vibratory motion directly to any fluid piped into said vessel including a piezoelectric element attached to said vessel, wherein said vibratory motion is transmitted through said any fluid to said device;
- means for selectively energizing an electrical device to be tested and an electromechanical device to be tested; and
- means for selectively draining said nay fluid within said vessel from said vessel.

39. An apparatus for testing electrical, electromechanical and mechanical devices comprising:
- a vessel in which a device to be tested is placed;
- a reservoir of below-zero degree Celsius fluid;
- a reservoir of above-zero degree Celsius fluid
- said below-zero degree Celsius fluid and said above-zero degree Celsius fluid differing in temperature by at least 40 degrees Celsius,
- means disposed between said vessel and each of said reservoirs for piping said below-zero degree Celsius fluid and said above-zero degree Celsius fluid between said reservoirs and said vessel;
- means for controlling the flow of said below-zero degree Celsius fluid and said above-zero degree Celsius fluid between said reservoirs and said vessel;
- means for transmitting vibratory motion directly to any fluid piped into said vessel including a transducer that is suspended within said vessel so that said any fluid placed within said vessel makes fluid contact with said transducer, wherein said vibratory motion is transmitted through said any fluid to said device;
- means for selectively energizing an electrical device to be tested and an electromechanical device to be tested; and
- means for selectively draining said any fluid within said vessel from said vessel.

* * * * *